US007060303B2

(12) United States Patent
Jones

(10) Patent No.: US 7,060,303 B2
(45) Date of Patent: Jun. 13, 2006

(54) USE OF PURSLANE TO TREAT FACIAL WRINKLES

(75) Inventor: Brian C. Jones, Warwick, NY (US)

(73) Assignee: Avon Products, Inc., New York, NY (US)

( * ) Notice: Subject to any disclaimer, the term of this patent is extended or adjusted under 35 U.S.C. 154(b) by 135 days.

(21) Appl. No.: 10/334,886

(22) Filed: Dec. 31, 2002

(65) Prior Publication Data

US 2004/0126352 A1    Jul. 1, 2004

(51) Int. Cl.
*A01N 65/00* (2006.01)
(52) U.S. Cl. ....................................... 424/725
(58) Field of Classification Search ................. 424/725
See application file for complete search history.

(56) References Cited

U.S. PATENT DOCUMENTS

| 4,379,454 A | 4/1983 | Campbell et al. ........... 604/897 |
| 4,820,724 A | 4/1989 | Nimni ........................ 514/396 |
| 4,956,171 A | 9/1990 | Chang ........................ 424/449 |
| 4,985,459 A | 1/1991 | Sunshine et al. ........... 514/561 |
| 5,223,262 A | 6/1993 | Kim et al. ................... 424/448 |
| 5,770,222 A | 6/1998 | Unger et al. ................ 424/450 |
| 5,824,312 A | 10/1998 | Unger et al. ............. 424/195.1 |
| 5,834,513 A | 11/1998 | Ptchelintsev et al. ....... 514/561 |
| 5,847,003 A | 12/1998 | Ptchelintsev et al. ....... 514/532 |
| 5,869,060 A * | 2/1999 | Yoon et al. .................. 424/725 |
| 6,153,208 A | 11/2000 | McAtee et al. ............. 424/402 |
| 6,338,855 B1 | 1/2002 | Albacarys et al. .......... 424/409 |
| 6,451,358 B1* | 9/2002 | Zhao ........................... 424/746 |
| 2001/0044422 A1* | 11/2001 | Zhao ........................... 514/53 |
| 2002/0081291 A1 | 6/2002 | Hawrot .................... 424/94.63 |

FOREIGN PATENT DOCUMENTS

| JP | 02000053557 | * | 2/2000 |
| KR | 2002001911 | * | 1/2002 |
| KR | 2002016960 | * | 3/2002 |
| KR | 2002093364 | * | 12/2002 |

OTHER PUBLICATIONS

D. S. Becker, "Muscle Recruitment as a Potential Side Effect of Botulinum Toxin Therapy," *Cosmetic Dermatology*, 15(12):35-36, Dec. 2002.
A. Blitzer, et al., "Botulinum Toxin for the Treatment of Hyperfunctional Lines of the Face," *Arch Otolaryngol Head Neck Surg*, 119:1018-1022, Sep. 1993.
J. D. A. Carruthers and J. A. Carruthers, "Treatment of Glabellar Frown Lines with C. Botulinum-A Exotoxin," *J. Dermatol Surg Oncol*, 18:17-21, 1992.
K. Chan, et al., "The analgesic and anti-inflammatory effects of *Portulaca oleracea* L. subsp. *sativa* (Haw.) Celak," *J. Ethnopharm.*, 73:445-451, 2000.
M. Grieve, "Purslane, Green—Purslane, Golden," *A Modern Herbal—The Medicinal, Culinary, Cosmetic and Economic Properties, Cultivation and Folklore of Herbs, Grasses,*

*Fungi, Shrubs and Trees With All Their Modern Scientific Uses*, 660-661, (Barnes & Noble Books 1996) (1931).
S. Habtemariam, et al., "The muscle relaxant properties of *Portulaca oleracea* are associated with high concentrations of potassium ions," *J. Ethnopharma.*, 40:195-200, 1993.
A. I. Mohamed & A. S. Hussein, "Chemical composition of purslane (*Portulaca oleracea*),"*Plant Foods for Human Nutrition*, 45:1-9, 1994.
Ki-Bong Oh, et al., "Detection of Antifungal Activity in *Portulaca oleracea* by a Single-cell Bioassay System," *Phytotherapy Res.*, 14:329-332, 2000.
F. Okwuasaba, et al., "Comparison Of The Skeletal Muscle Relaxant Properties Of *Portulaca oleracea* Extracts With Dantrolene Sodium And Methoxyverapamil," *J. Ethnopharm.*, 20:85-106, 1987.
F. Okwuasaba, et al., "Investigation Into The Mechanism Of Action Of Extracts Of *Portulaca oleraca*," *J. Ethnopharm.*, 21:91-97, 1987.
F. Okwuasaba, et al. "Skeletal Muscle Relaxant Properties Of The Aqueous Extract of *Portulaca oleracea*," *J. Ethnopharm.*, 17:139-160, 1986.
O. Parry, et al., "Effect of An Aqueous Extract Of *Portulaca oleracea* Leaves On Smooth Muscle And Rat Blood Pressure," *J. Ethnopharm.*, 22:33-44, 1988.
O. Parry, et al., "Preliminary Clinical Investigation Into The Muscle Relaxant Actions Of An Aqueous Extract Of *Portulaca oleracea* Applied Topically,"*J. Ethnopharm.*, 21:99-106, 1987.
O. Parry, et al., "Skeletal Muscle Relaxant Action Of An Aqueous Extract Of *Portulaca oleracea* In The Rat," *J. Ethnopharm.*, 19:247-253, 1987.
O. Parry, et al., "The skeletal muscle relaxant action of *Portulaca oleracea*: role of potassium ions," *J. Ethnopharm.*, 40:187-194, 1993.
M. B. Quinlan, et al., "Ethnophysiology and herbal treatments of intestinal worms in Dominica, West Indies," *J. Ethnopharm.*, 80:75-83, 2002.
R. Radhakrishnan, et al., "Neuropharmacological actions of *Portulaca oleraceae* L v. sativa (Hawk)," *J. Ethnopharm.*, 76:171-176, 2001.
O. P. Verma, et al., "Antifertility effects of common edible *Portulaca oleracea* on the reproductive organs of male albino mice," *Indian J. Med. Res.*, 75:301-310, Feb. 1982.
G. C. Yen, et al., "Evaluation of the cytotoxicity, mutagenicity and antimutagenicity of emerging edible plants," *Food and Chemical Toxicology*, 39:1045-1053, 2001.

* cited by examiner

*Primary Examiner*—Michael Meller
(74) *Attorney, Agent, or Firm*—Anthony M. Santini; Charles J. Zeller; Joan M. McGillycuddy

(57) ABSTRACT

The invention relates to topical compositions containing components of plants from the Purslane family and methods for improving the aesthetic appearance of skin, particularly, preventing, ameliorating, treating and/or reducing fine lines and/or wrinkles. More particularly, the present invention relates to the use of topical compositions containing extract from the *Portulaca oleracea* plant to treat signs of dermatological aging, especially facial lines and deep wrinkles, and/or improve the aesthetic appearance of the skin. Preferably, the composition is applied once daily to the skin.

12 Claims, No Drawings

USE OF PURSLANE TO TREAT FACIAL WRINKLES

BACKGROUND OF THE INVENTION

1. Field of the Invention

The present invention relates to the novel use of plants from the Purslane family in cosmetic products for the face or body. More particularly, the present invention relates to the use of topical compositions having a Purslane plant component to treat, including prevent, ameliorate and/or reduce, signs of dermatological aging, especially wrinkles, and/or improve the aesthetic appearance of skin. The most preferred plant component is from the *Portulaca oleracea* (a.k.a. "green purslane") plant. Still more particularly, the present invention provides the beneficial effects of substances such as *Botulinum* toxin without the toxicity or other adverse physiological effects associated with long-term use of such substances.

2. Description of the Prior Art

The Purslane plant family includes various plants, including *Portulaca oleracea* (a.k.a. "green purslane"), *Portulaca sativa* (a.k.a. "golden purslane"), and *Atriplex portulacoides* (a.k.a. "sea purslane").

The plant *Portulaca oleracea* Linn. (family: Portulacaceae) belongs to a genus of succulent annuals commonly distributed all over the world in moderate to warm climates, including many parts of Europe, United States, Africa, East and West Indies, China, Japan, and the Middle East. Common names for *P. oleracea* include, but are not limited to, Purslane, Pigweed, Munyeroo, Thukouro, Lifa, Coupier, Little Hogweed, and Perpine. In West Africa, the juice and aqueous extracts from this plant were commonly used to treat various illnesses such as swelling, whitlow, bruises, boils, earache, toothache, swelling, abscesses (topical) and as a vermifuge and diuretic (Okwuasaba et al., 1986). The leaves, macerated in water, are even considered to be a useful heart "tonic."

The Golden Purslane (*Portulaca sativa*) is a variety of Purslane with yellow leaves, less hardy than green purslane, but possessing the same qualities. The seeds of an individual plant have been known to produce both green and golden leaves. Other species of Purslane plants include, Sea Purslane (*Atriplex portulacoides*), commonly found along the sea shores of England and Ireland. It grows in salt marshes and muddy foreshores. Grieve's *A Modern Herbal* describes its foliage as pointed and lance-head in form, and silvery white in color.

A review of the records for folklore and scientific uses of *Portulaca oleracea* indicate that this species has had many medicinal uses. These activities include significant anti-inflammatory and analgesic effects (Chan et al., 2000), antimutagenicity (Yet et al., 2001), antifungal (Oh et al., 2000), antifertility (Verma et al., 1982), reduced cancer and heart disease (Mohamed et al., 1994), controlling intestinal worms and parasites (Quinlan et al., 2002). It has also been listed by Grieve's *A Modern Herbal* for application towards strangury, dry cough, shortness of breath, immoderate thirst, inflammation and sores, hot agues, want of sleep, all pains in the head proceedings from the heat, and the frenzy.

*Portulaca oleracea* has also been used for the treatment of cancer (U.S. Pat. No. 5,869,060, Yeon et al., issued Feb. 9, 1999), as an anti-microbial and antifungal active (U.S. Pat. No. 6,338,855, Albacarys et al., issued Jan. 15, 2002), and as a non-steroidal cosmetic soothing active (U.S. Pat. No. 6,153,208, McAtee et al., issued Nov. 28, 2000), as a sunscreen agent from natural sources (U.S. Pat. No. 5,824,312, Unger et al., issued Oct. 20, 1998), and as an antidiabetic agent to control blood sugar levels (JP. Pat. No. 63,208,531, Kin et al., published Aug. 30, 1988). It has also been referenced for the use as cosmetic soothing agents (U.S. Pat. No. 4,985,459, Sunshine et al., issued Jan. 15, 1991). However, none of these patents disclose the use of *Portulaca oleracea* for the treatment of fine lines and wrinkles. In addition, the properties of *Portulaca oleracea* as a muscle relaxant have also been studied (Okwuasaba et al., 1986, Okwuasaba et al., 1987(1), Okwuasaba et al., 1987(2), Okwuasaba et al., 1987(3), Parry et al., 1987(1), Parry et al., 1987(2), Parry et al., 1988, Parry et al., 1993, Habtemarin et al., 1993, Radhakrishnan et al., 2001). Again, none of these studies report the use of Portulaca for reducing facial lines and wrinkles as directed by this application.

*Botulinum* toxin (also known by the tradename, Botox®, Allergen, Irvine, Calif.), is currently in vogue for treating wrinkles and fine lines, and acts on states of muscular spasticity by specifically inhibiting neurotransmission in nerve cells, thereby causing contracted muscles to relax (e.g., A. Blitzer et al., 1993; U.S. Pat. No. 6,344,461 B1 to L. Breton et al.). This toxin has been found to act on wrinkles of the glabella (wrinkles between the eyebrows) when injected subcutaneously, (see, J. D. Carruthers, 1992; U.S. Pat. No. 6,344,461 B1 to L. Breton et al.). However, the full extent of adverse effects related to long-term use of *botulinum* toxin and products or treatments containing this material are still not well established. *Botulinum* toxin treatment has been associated with a number of side effects including, transient fatigue, dysphagia, neck weakness, hoarseness, and localized pain. In addition, many patients who preliminarily respond to *botulinum* toxin, subsequently become non-responsive to treatment or exhibit muscle recruitment at the treatment site (where paralysis of a set of muscles leads to recruitment of other muscle groups in an attempt to counteract the paralysis, thereby causing wrinkles to actually become more prominent) (see, for instance, Becker, 2002; U.S. Patent. No. US2002/00812914 to Hawrot).

Therefore, safe, effective and new components of compositions to treat, prevent, reduce, inhibit, and/or improve the dermatological signs of aging, would be advantageous for the formulation of treatments and products for the skin. To date, there has not been an efficacious topical composition for the treatment of fine lines and wrinkles that contains a Purslane plant component. As described herein, novel and beneficial methods and compositions, as well as their mode of action, for the treatment of wrinkles and the like, as well as for personal care products for the skin, are provided by the present invention.

SUMMARY OF THE INVENTION

It is an aspect of the present invention to provide a topical composition having a component of a plant from the Purslane family in cosmetic products for the face and body.

It is another aspect of the present invention to provide a topical composition having extract isolated from the *Portulaca oleracea* plant to treat, including prevent, ameliorate and/or reduce, signs of dermatological aging, especially wrinkles due to hyperkinetic activity of facial muscles, and/or improve the aesthetic appearance of skin, and methods of its use. Topical compositions containing components of other species of Purslane plants are also contemplated by the present invention including, but not limited to, *Portulaca sativa* and *Atriplex portulacoides*.

It is a further aspect of the present invention to provide a method of treating fine lines and/or wrinkles, comprising applying to skin a topical, composition having an amount of a component from a Purslane plant effective to prevent, ameliorate and/or reduce fine lines and/or wrinkling.

It is yet another aspect to provide a method for delivering the benefits of substances such as *Botulinum* toxin, without the toxicity or other undesirable side effects associated with such substances.

These and other aspects and advantages of the present invention are achieved by a topical composition that contains a component of a Purslane plant. In a preferred embodiment, the component is an extract isolated from the *Portulaca oleracea* plant in an effective amount, preferably in an amount of about 0.005 wt % to about 20 wt %, based on the total weight of a composition.

DETAILED DESCRIPTION OF THE INVENTION

The present invention relates to the discovery that components from Purslane plants diminish facial skin lines and wrinkles, especially wrinkling due to hyperkinetic activity of facial muscle, in a topical cosmetic, drug, composition, or formulation. According to the present invention, the component is preferably in the form of an extract from a Purslane plant, most preferably the *Portulaca oleracea* plant, that when administered topically, has the distinct activity of relaxing facial skeletal muscle, thereby "relaxing" the skin in the face to lessen deep facial lines and wrinkles.

Although the use of this invention is similar to the cosmetic use of subcutaneously-injected *botulinum* toxin, which reduces facial lines and wrinkles by relaxing facial muscles, its application (topical), mechanism of action, and non-toxic physiological effects are unique and unexpected compared to *botulinum* toxin. Moreover, *botulinum* toxin is not effective when administered topically, and localization of the toxin upon injection may be difficult to control, increasing the risk that the toxin will migrate to undesired areas. In contrast, the component(s) of Purslane plants are effective when applied topically, and, without wishing to be bound by theory, exert their muscle relaxant effects, not by blocking neurotransmission of nerve cells as *botulinum* toxin, but rather, through a mechanism of action involving the high concentrations of potassium, calcium, and other components and/or constituents present in the plants that are thought to interfere with the intracellular signaling functions of skeletal muscle tissues (Parry et al., 1998; Habetemariam et al., 1993; Radhakrishan et al., 2001). Topical application of the Purslane plant components also facilitates the targeted delivery of the active components without the requirement of an injection or the expertise of a health practitioner.

The present invention, therefore, provides novel compositions and methods using components of Purslane plants, preferably in the form of a *Portulaca oleracea* extract, which are newly found to be effective to treat, including prevent, ameliorate, and/or reduce, signs of dermatological aging, especially wrinkling and/or improve the aesthetic appearance of the skin upon daily application to skin.

1. Compositions Comprising Purslane Plants

For purposes of the invention, the Purslane plant may be in any form including, but not limited to, the whole plant, a dried plant, a ground plant, an extract, a dried extract, a synthetic extract, or components and/or constituents found in, or isolated from, the plants, and/or portions of the plants, or extracts derived either directly or synthetically from the plants, or any combinations thereof In a preferred embodiment, the present compositions preferably have a concentration of Purslane plant of about 50 µg/g to about 200 mg/g. More preferably, the concentration would range from about 50 mg/g to about 150 mg/g. These concentrations are based upon whole plant preparations (i.e., if the whole plant, or a dried plant, is ground and then incorporated into the composition).

Alternatively, if a dried extract is prepared according to methods known in the art (see, for instance, Example 1), then approximately $\frac{1}{10}^{th}$ of solids (i.e., about 5 µg/g to about 20 mg/g) could be used. However, if 50 µg of an aqueous extract that consists of 85% solvent is used, then the percentage active would be too low. Accordingly, one of ordinary skill in the art would know to adjust the amount of extract used based upon the percentage of solvent. In addition, with respect to the upper end of the range, it may be possible to exceed the upper limit, but doing so may result in a case of "diminishing returns." One of ordinary skill in the art would be able to adjust the amount of extract used based upon the specific application or effect desired. To provide additional guidance to those skilled in the art for practicing the present invention, the present compositions preferably have an amount of the Purslane plant from 0.005 wt % to about 20 wt %, of the total weight of the composition. More preferably, the present compositions have an amount of the Purslane plant from about 5 wt % to about 15 wt %. The efficacy of the Purslane plant concentration in a topical composition is approximately equivalent to $10^{-1}$ concentration of Purslane plant percent by weight of the composition. For example, to provide the efficacy of about 0.1 wt % (based upon the total weight of the composition) Purslane plant activity, a composition of the present invention preferably includes about 1 wt % of the Purslane plant.

In another embodiment, the Purslane plant extract as used herein, also includes "synthetic" extracts, i.e. various combinations of known Purslane plant components and/or constituents that are combined to substantially mimic the composition and/or activity of a Purslane plant extract of natural origin. Such synthetic extracts are included in the term "Purslane plant extract". The synthetic extracts will have at least one discrete component or active ingredient in common with a Purslane plant. More preferably, the synthetic extracts will have two or more, three or more, or four or more active ingredients in common with a Purslane plant. Most preferably, the synthetic extracts will have substantially the same number of active ingredients as a natural extract. The correspondence of the numerical incidence of active ingredients between the synthetic extracts and the plant or a natural extract may also be described in terms of "percent commonality". Preferably, the synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract. The plant or natural extract for comparison is derived, most preferably, from the *Portulaca oleracea* plant.

As stated above, the preferred components for use in the present invention are from the *Portulaca oleracea* plant. However, it is also contemplated that other members of the Purslane plant family may work equally as well including, but not limited to, *Portulaca sativa* and *Atriplex portulacoides*.

For use in the compositions of this invention, the Purslane plants or components and/or active constituents are preferably derived directly from the plants. The components may be in a pure form, a semi-pure form, or unpurified form. In a preferred embodiment, the components are in the form of an extract obtained by aqueous and/or hydroalcoholic solvent extraction (Example 1).

In accordance with this invention, the components from the Purslane plant comprise compositions which include, without limitation, topically applied formulations, anti-oxidants, anti-inflammatories, sunscreens, cosmetics, including makeups, anti-aging formulations, e.g., creams for fine lines and/or wrinkles, topicals, skin penetration enhancers, and the like. Also in accordance with this invention, the Purslane plant components and additional ingredients comprising such compositions can be formulated in a variety of product forms. Preferably, the compositions are prepared in targeted delivery systems, e.g. creams, lotions, gels, serums, transdermal patches, and the like, particularly for topical administration. Targeted delivery and/or penetration enhancement may also be achieved by iontophoresis.

The present invention further provides the compositions comprising the Purslane plant components preferably for topical administration or for targeted delivery without inducing significant irritation. Thus, the inventive compositions are especially suitable for sensitive skin. The compositions are applied to the skin for a period of time sufficient to improve the aesthetic appearance of skin. The compositions are preferably applied topically once or twice daily. The daily application is preferably for a period of one week, two weeks, four weeks, or more. The compositions can be formulated into liposomes which can comprise other additives or substances, and/or which can be modified to more specifically reach or remain at a site following administration.

The present invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, preferably as a lotion or cream, but also in an anhydrous or aqueous base, as well as in a sprayable liquid form. Other suitable cosmetic product forms for the compositions of this invention include, for example, an emulsion, a lip balm, a lip gloss, a lotion, a mask, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, and the like, as well as other botanicals such as aloe, chamomile, and the like, and as further described below.

The compositions of the present invention yield improvements to the aesthetic appearance of the skin by treating at least one of the following: dermatological aging, especially chronological, actinic or hormonal aging. In particular, improvements to the aesthetic appearance of skin include at least one of the following: makes facial lines appear less noticeable, makes facial lines and/or wrinkles feel plumped, improves appearance of suborbital lines and/or periorbital lines, improves appearance of crow's feet, reduces and/or diminishes the appearance of wrinkles, particularly facial wrinkles on the cheeks, forehead (e.g. perpendicular wrinkles between the eyes, horizontal wrinkles above the eyes) and/or around the mouth (e.g. marionette lines), and particularly deep wrinkles or creases, rejuvenates and/or revitalizes skin, particularly aging skin, decreasing hyperkinetic facial wrinkling and reduces and/or eliminates fine and/or deep lines.

Also, embraced by the present invention are transdermal modes of delivery, such as patches and the like, with or without a suitable penetration enhancers. The methods and compositions embodied by the invention provide a means by which the Purslane components can be effectively administered in a transdermal system. Accordingly, a transdermal means of delivering a composition or formulation (often with a penetration enhancing composition) to the skin is that of the transdermal patch or a similar device as known and described in the art. Examples of such devices are disclosed in U.S. Pat. Nos. 5,146,846, 5,223,262, 4,820,724, 4,379,454 and 4,956,171; such descriptions are not meant to be limiting. The transdermal mode of storing and delivering the compositions onto the skin and forming the active composition is convenient and well suited for the purposes of an embodiment of the present invention. In a preferred method, the application is through a sustained release vehicle, e.g., a topically applied sustained released patch. Preferably, when a topical patch is used, the patch is applied to the desired area for extended period of time. Preferably, the extended period of time is greater than one hour, most preferably the extended period of time is overnight, i.e., when the user is sleeping.

Another particular embodiment of the present invention is directed to the delivery of the described compositions by the use of targeted delivery systems, for example, liposomes, microspheres (see, e.g., U.S. Pat. No. 5,770,222 to Unger et al.), and the like, so that the Purslane components and/or active constituents can more readily reach and affect the muscle layer of the area of application, e.g., face or neck, or the other area of the skin.

In another preferred embodiment, the topical compositions of the present-invention also include at least one of the following: a skin penetration enhancer, a surface smoother, a skin plumper, an optical diffuser, a sunscreen, an exfoliation promoter, and an antioxidant.

A surface smoother provides the functional benefits of enhancing skin smoothness and reducing the appearance of fine lines and coarse wrinkles. Examples include isopropyl myristate, petrolatum, isopropyl lanolate, silicones (e.g., methicone, dimethicone), or any mixtures thereof. The surface smoother is preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 wt % to about 20 wt % of the total weight of the composition.

A sunscreen protects the skin from damaging ultraviolet rays. In an illustrative embodiment of the present invention, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 wt % to about 30 wt % of the total weight of the composition. The addition of a sunscreen may prevent/reduce the photodegradation of the composition while in the package as well as serve to protect the skin from ultraviolet radiation.

The compositions of the present invention having sunscreen bring about additional improvements to the aesthetic appearance of skin, including at least one of the following: minimizes sunburning, minimizes tanning, and reduces redness.

The present compositions may also have one or more exfoliation promoters. Suitable examples of an exfoliation promoter that can be used in the present compositions include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof.

When the present invention includes an exfoliation promoter, the composition has about 0.5 wt % to 30 wt %, preferably about 1 wt % to about 15 wt %, more preferably about 4 wt % to about 10 wt %, and most preferably about 4 wt %, of the exfoliation promoter based on the total weight of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or nonreduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 wt % to about 10 wt %, and more preferably from about 0.001 wt % to about 5 wt %, of the total weight of the composition.

The present composition may also have one or more of the following active agents, ingredients or adjuvants: anesthetics, anti-allergenics, antifungals, antiseptics, chelating agents, colorants, demulcents, emollients, emulsifiers, fragrances, humectants, lubricants, moisturizers, pH adjusters, pigment altering agents, preservatives, stabilizers, surfactants, thickeners, viscosity modifiers, vitamins, or any mixtures thereof. The amounts of these various substances are those that are conventionally used in the cosmetic or pharmaceutical fields, for example, they can constitute from about 0.01% to 20% of the total weight of the composition.

Nonlimiting examples of active agents for formulating into the compositions of the present invention include those reagents having an effect on the treatment of wrinkles and/or fine lines, in addition to the Purslane actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.0001% to 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

The Purslane plant component(s) of the present invention are preferably contained in a cosmetically or dematologically acceptable vehicle, medium, diluent or carrier.

In an embodiment embracing topical application, the compositions of this invention comprise a medium (vehicle, diluent or carrier) that is compatible with human skin. The compositions can be formulated as aqueous, alcohol, or aqueous/alcohol-based solutions, ointments, lotions, gels, water-in-oil, oil-in-water, of water-oil-water triple emulsions having the appearance of a cream or gel, microemulsions, or aerosols. In addition, the compositions can be in the form of vesicular dispersions containing ionic and/or nonionic lipids, as described above. Dosage units suitable for such compositions are formulated according to the conventional knowledge and techniques used in the art.

More particularly, the compositions for topical application can be in the form of a protective care composition for the skin, preferably for the face, the neck, the hands, the feet, or other areas of the body. Nonlimiting examples include day creams or lotions, night creams or lotions, sunscreen creams, lotions, or oils, body milks, makeup (a foundation), artificial tanning compositions, depilatories, and patches.

Emulsifiers are typically present in the compositions of the invention in an amount of about 0.1% to 30%, by weight and preferably from about 0.5% to 30% by weight relative to the total weight of the composition. However, not all compositions will necessarily include emulsifiers.

2. Methods of Use of Purslane Plants

In another embodiment, the present invention encompasses a method of treating fine lines, wrinkles, and/or other dermatological effects of aging, photoexposure of skin and, especially wrinkling hyperkinetic activity of facial muscles, comprising applying to skin a composition containing at least one component of a Purslane plant. In a specific embodiment, the component is in an extract of *Portulaca oleracea* in a cosmetically and/or dermatologically acceptable medium, and in an amount effective to treat, reduce, prevent and/or ameliorate fine lines, wrinkles and/or other dermatological effects of aging of skin. The application of the Purslane component containing composition is preferably topical.

Another embodiment of the present invention relates to a method of improving the aesthetic appearance of skin and comprises applying to the skin, or introducing via a directed mode of delivery, a composition including one or more Purslane components in an amount effective to improve the aesthetic appearance of the skin. Dermatological aging can include chronological aging, actinic aging, hormonal aging, or any combination thereof.

As will be appreciated by the practitioner, cosmetic treatments comprising compositions containing the Purslane plant components and/or constituents of the invention can be carried out, for example, by topically applying the cosmetic composition as described herein according to the routine technique for administering such compositions. Routine and commonly practiced techniques encompass the application of creams, lotions, gels, sera, ointments, patches, makeups, makeup-removing milks, or sunscreen compositions to the skin; spraying as a form of application is also envisioned.

EXAMPLES

The following examples describe specific aspects of the invention to illustrate the invention and provide a description of the present methods for those skilled in the art. The examples should not be construed as limiting the invention, as the examples merely provide specific methodology useful in the understanding and practice of the invention and its various aspects.

Example 1

A Purslane plant extract of the present invention can be extracted from natural raw materials by using the methods of aqueous-organic solvent extraction as is well known in the art. One such extraction process is set forth below.

Preparation of Extract

The following describes a suitable method of preparing an extract useful for preparing a composition of the present invention.

A method of preparation for an aqueous extract from fresh stem and leaves as described in Parry et al., 1986, which is incorporated herein by reference, may be used. Freshly collected plants are washed and dried by blotting. The blotted dry plants are then ground to a paste. The ground paste is then extracted with 6 times its weight in water at 100° C. for 6 to 8 hours. Water may then slowly evaporated under vacuum at 40° C. to form a dried material. This dried material may then added to water phase during formulation of the cosmetic product.

Example 2

Clinical Evaluation of Cosmetics Containing *Portulaca oleracea* Extract

The safety and efficacy of topically administered extract from a *Portulaca oleracea* plant is studied in humans after a single-dose administration of a cosmetic formulation. Ten to fifteen panelists (preferably between 35 and 50 years old) with mild to moderate forehead lines and wrinkles are selected. Panelists initially have a skin replicate made to establish a baseline depth and severity of wrinkles. On the following day, study technicians apply 0.6 grams of product (at an extract concentration of 140 mg/g) over an approximate 6 cm$^2$ semi-occlusive patch area on the subject's foreheads. The product formulation preferably consists of a formulation designed to increase the penetration of water-soluble materials. The product remains on the subject for one hour. After the one hour exposure, a repeat skin replicate is taken to assess changes from the previous day. For example, a layer of a flexible "non-cured" material, such as latex, is applied to the skin. Upon removal of the "cured" material from the skin, the side that was adjacent to the skin is assessed, either visually or via instrumentation, to determine if there has been a change in number or depth of wrinkles. In addition, panelists are asked to contract the forehead skin and brow to determine the overall efficacy and potency of the formulation. Other dermatological tests are known in the art for testing the efficacy of an anti-wrinkling composition. Any such test would be useful as well.

The content of all patents, patent applications, published articles, abstracts, books, reference manuals and abstracts, as cited herein are hereby incorporated by reference in their entireties to more fully describe the state of the art to which the invention pertains.

It should be understood that the foregoing description is only illustrative of the present invention. Various alternatives and modifications can be devised by those skilled in the art without departing from the invention. Accordingly, the present invention is intended to embrace all such alternatives, modifications and variations that fall within the scope of the appended claims.

REFERENCES

1. Becker, D S, Muscle Recruitment as a Potential Side Effect of *Botulinum* Toxin Therapy. *Cosmetic Dermatology. December* 2002; 15(12): 35–36.
2. Blitzer A. et al., *Arch. Otolaryngol. Head Neck Surg.* 1993; 119:118–122.
3. Carruthers J D, *J. Dermatol. Surg. Oncol.* 1992; 18:17–21.
4. Chan et al., 2000.
5. Grieve M, *A Modern Herbal*, The Medical, Culinary, Cosmetic and Economic Properties, Cultivation And Folklore Of Herbs, Grasses, Fungi, Shrubs And Trees With All Their Modern Scientific Uses, Barnes & Noble, Inc.; Revised Edition, 1996, pp. 660–661.
6. Habtemariam et al., The Muscle Relaxant Properties Of *Portulaca Oleracea* Are Associated With High Concentrations Of Potassium Ions. *J. Ethnopharmacology* 1993; 40: 195–200.
7. Mohamed et al., 1994.
8. Oh et al., 2000.
9. Okwuasaba et al., Skeletal Muscle Relaxant Properties Of The Aqueous Extracts Of *Portulaca Oleracea*. *J. Ethnopharmacology* 1986; 17: 139–160.
10. Okwuasaba et al, Comparison Of The Skeletal Muscle Relaxant Properties Of *Portulaca Oleracea* Extracts With Dantrolene Sodium And Methoxyverapamil. J. Ethnopharmacology 1987; 20: 85–106.
11. Okwuasaba et al, Investigation Into The Mechanism Of Action Of Extracts Of *Portulaca Oleacea*. *J. Ethnopharmacology* 1987; 21: 91–97.
12. Parry et al., Preliminary Clinical Investigation Into The Muscle Relaxant Actions Of An Aqueous Extract Of *Portulaca Oleracea* Applied Topically; *J. Ethnopharmacology* 1987; 21: 99–106.
13. Parry et al., Skeletal Muscle Relaxant Action Of An Aqueous Extract Of *Portulaca Oleancea* In The Rat. *J. Ethnopharmacology,* 1987; 19: 247–253.
14. Parry et al., Effect Of An Aqueous Extract Of *Portulaca Oleracea* Leaves On Smooth Muscle And Rat Blood Pressure. *J. Ethnopharmacology,* 1988; 22: 33–44.

15. Parry et al., The Skeletal Muscle Relaxant Action Of *Portulaca Oleracea*: Role Of Potassium Ions. *J. Ethnopharmacology*, 1993; 40: 187–194.
16. Parry et al., 1998.
17. Quinlan et al., 2002.
18. Radhakrishnan et al., Neuropharmacological Actions Of *Portulaca Oleraceae* L. v. *sativa*. *J. Ethnopharmacology*, 2001; 76: 171–176.
19. Verma et al., 1982.
20. Yet et al., 2001.

What is claimed is:

1. A method of improving the aesthetic appearance of skin comprising topically applying to skin a composition comprising an aqueous extract of a Purslane plant in an amount effective to improve the aesthetic appearance of skin selected from the group consisting of:
   decreasing the number of facial lines, wrinkles, creases or folds;
   decreasing the depth of a facial line, wrinkle, crease or fold;
   decreasing the number of hyperkinetic facial lines, wrinkles, creases or folds; and
   decreasing the death of a hyperkinetic facial line, wrinkle, crease, fold and a combination thereof.

2. The method of claim 1, wherein said composition is applied for a period of time sufficient to improve the aesthetic appearance of skin.

3. The method of claim 1, wherein said applying of the composition occurs at least once daily for a period of time sufficient to improve the aesthetic appearance of skin.

4. The method of claim 1, wherein the skin is on the face.

5. The method of claim 1, wherein the Purslane plant is selected from the group consisting of *Portulaca oleracea, Portulaca sativa, Atriplex portulacoides*, and any combination thereof.

6. The method of claim 1, wherein the Purslane plant is *Portulaca oleracea*.

7. The method of claim 1, wherein the aqueous extract of the Purslane plant is present in an amount from about 0.005 wt % to about 10 wt % based upon the total weight of the composition.

8. The method of claim 1, wherein the aqueous extract of the Purslane plant is present in an amount from about 0.01 wt % to about 7 wt % based upon the total weight of the composition.

9. The method of claim 1, wherein the aqueous extract of the Purslane plant is present in an amount from about 0.05 wt % to about 2.0 wt % based upon the total weight of the composition.

10. The method of claim 1, wherein topically applying to skin comprises a transdermal patch application.

11. The method of claim 1, wherein topically applying to skin comprises a targeted delivery system.

12. The method of claim 1, wherein topically applying to skin comprises application in a form selected from the group consisting of a cream, a lotion, a gel, a serum, an ointment, an oil, a foundation, a depilatory, a patch and spraying.

* * * * *